United States Patent [19]

Fitzgerald

[11] Patent Number: 4,514,062
[45] Date of Patent: Apr. 30, 1985

[54] INSTRUMENT FOR INDIRECT OPHTHALMOSCOPY AND ELECTRICAL ENERGY PRODUCING MEANS THEREFOR

[76] Inventor: James L. Fitzgerald, 20 Mason St., Williamstown, Mass. 01267

[21] Appl. No.: 366,698

[22] Filed: Apr. 8, 1982

[51] Int. Cl.³ ............................................. A61B 3/10
[52] U.S. Cl. ................................. 351/205; 351/218; 351/221
[58] Field of Search ................ 351/205, 221, 218; 429/96, 99, 100; 354/62

[56] References Cited

U.S. PATENT DOCUMENTS

| | | |
|---|---|---|
| 2,757,574 | 8/1956 | Thorburn . |
| 3,441,340 | 4/1969 | Moore et al. . |
| 3,582,191 | 6/1971 | Cohen . |
| 3,586,414 | 6/1971 | Schultz . |
| 3,664,730 | 5/1972 | Cardona . |
| 3,685,887 | 8/1972 | Spurney . |
| 3,847,470 | 11/1974 | Dederer et al. . |
| 3,881,812 | 5/1975 | Ben-Tovim . |
| 3,945,712 | 3/1976 | Crock et al. . |
| 3,963,329 | 6/1976 | Stumpf ............................... 351/205 |
| 4,015,898 | 4/1977 | Schirmer . |
| 4,220,401 | 9/1980 | Muchel . |
| 4,279,478 | 7/1981 | Matsumura ........................ 351/206 |

Primary Examiner—Rodney B. Bovernick
Attorney, Agent, or Firm—Sixbey, Friedman & Leedom

[57] ABSTRACT

An ophthalmoscope for observing the fundus of an eye includes a casing, a light source for illuminating the fundus, lens means for viewing the illuminated fundus, electrical energy producing means for providing electrical energy to the light source and means electrically connecting the electrical energy producing means and the light source, the electrical energy producing means being supported on, extending substantially completely around and substantially conforming to the outer surface of the casing. Desirably, the electrical energy producing means is a battery having at least one battery section, each battery section including at least two substantially annular contact members and a plurality of battery cells arranged in spaced relation and disposed between and electrically connected to the contact members. The cells within each battery section are electrically connected in parallel and adjacent battery sections are electrically connected in series.

23 Claims, 8 Drawing Figures

INSTRUMENT FOR INDIRECT OPHTHALMOSCOPY AND ELECTRICAL ENERGY PRODUCING MEANS THEREFOR

DESCRIPTION

1. Technical Field

The present invention relates to light projecting instruments for indirect ophthalmoscopy and, more particularly, to such instruments which are lightweight, battery powered, easy to handle and readily portable.

2. Background Art

In the widely used conventional method of indirect ophthalmoscopy an instrument consisting of an illuminating lamp, a projection system for directing a beam of illuminating light onto the fundus of a patient's eye and a binocular viewer for directing the fundus image to the observer's eyes is head mounted on a bracket worn by the observer. The illuminating light is projected from the head mounted lamp via a condensing lens hand held by the observer through the pupillary aperture onto the fundus. The fundus image is directed back to the binocular viewer through the pupillary aperture and the condensing lens. The image viewed by the observer using this type of ophthalmoscope is generally reversed and inverted. Much has been made of the supposed inconvenience associated with viewing a reversed and inverted image and of the effort required to mentally transpose the image during eye examinations and surgical operations and optical systems comprising various prismatic and mirror arrangements have been devised to convert the reversed and inverted image to an unreversed and erect image. However, experience has indicated that, in fact, there is very little need for ophthalmoscopes having reversing and/or erecting prisms for the simple reason that most experienced observers have become so accustomed to viewing reversed and inverted images that it is more confusing than helpful for them to now view unreversed and erect images.

The real problems associated with conventional indirect ophthalmoscopy are the physical burdens on the observer caused by the head-mounted ophthalmoscope particularly during lengthy examinations or surgical procedures. Most head-mounted ophthalmoscopes are too heavy and generate too much heat to be comfortably worn by the observer. Moreover, in use, the illuminating light has to be projected through the hand held lens and into the pupillary aperture by adjusting the head position of the observer—oftentimes requiring the head to assume unnatural and uncomfortable positions. As one solution to these problems it has been suggested to utilize hand-held ophthalmoscopes which incorporate within a single casing most or all of the illuminating, projecting and binocular viewing components needed in conventional ophthalmoscopy. While hand-held instruments relieve the heat and illuminating light-lens alignment problems associated with head mounted ophthalmoscopes such hand-held units are unrealistically heavy and cumbersome, particularly when it is appreciated that some eye examinations and/or surgical procedures require the observer to hand hold the ophthalmoscope for an hour or more. Moreover, virtually all presently known ophthalmoscopes, whether head-mounted or hand-held, are connected via an electrical or optical cable to a remote power or light source. This need for a cable and remote power or light source significantly detracts from the portability of the ophthalmoscope and severely limits its usefulness in other than office or operating room environments. The hand-held ophthalmoscopes described and claimed in the following patents are illustrative of ophthalmoscopes which suffer from one or more of the aforementioned disadvantages. U.S. Pat. No. 3,664,730—Cardona; U.S. Pat. No. 3,685,887—Spurney; U.S. Pat. No. 3,847,470—Dederer et al; U.S. Pat. No. 3,881,812—Ben-Tovim; U.S. Pat. No. 4,220,401—Muchel. Attempts have been made to increase the portability of hand-held instruments for ophthalmoscopy by providing internal battery power. However, the battery power units are so cumbersome and heavy that the instruments cannot easily be hand-held for the duration of prolonged examinations or surgical procedures. U.S. Pat. Nos. 3,441,340—Moore and 4,220,401—Muchel are exemplary of such instruments which disclose the use of a lengthy handle portion to house a plurality of flashlight-type, end-to-end series arranged battery power sources.

Accordingly, the present invention is directed to overcoming one or more of the problems set forth above and, particularly, to enhancing the portability of instruments for indirect ophthalmoscopy by providing an improved form of instrument which is lightweight, compact and internally powered.

DISCLOSURE OF THE INVENTION

In one aspect of the present invention this is accomplished by providing an ophthalmoscope for observing the fundus of an eye including a casing having an image receiving aperture and an image viewing aperture, illuminating means including a light source for emitting a light beam for illuminating the fundus, lens means for viewing the illuminated fundus and electrical energy producing means for providing electrical energy to the light source. The electrical energy producing means is removable and conforms to the outer surface of a section of the casing on which it is supported.

In another aspect of the present invention an instrument for indirect ophthalmoscopy is provided which is internally powered by a substantially annular battery comprising first and second substantially annular contact members and a plurality of battery cells arranged in spaced relation and disposed between and electrically connected to the contact members.

In a particularly preferred aspect of the present invention, there is provided an ophthalmoscope in which the image receiving and viewing apertures are arranged along a direct line of sight comprising the optical axis of the casing, a convex lens is mounted in the casing near the image receiving aperture and the fundus illumination means includes a semi-transparent mirror mounted near the image viewing aperture, the mirror being oriented to intercept and reflect the emitted light beam in order to direct the light beam substantially parallel to the optical axis of the casing through the lens and onto the fundus of an eye.

In still another aspect, the present invention comprehends a light projecting device comprising a casing including a light source for emitting a beam of light, means in the casing for permitting transmission of at least a portion of the light beam out of the casing and electrical energy producing means for providing electrical energy to the light source, the electrical energy producing means extending substantially completely around and substantially conforming to the outer surface of a section of the casing.

In yet another aspect, the present invention is directed to an electrical energy producing means in the form of a substantially annular battery including first and second substantially annular contact members and a plurality of battery cells arranged in spaced relation and disposed between and electrically connected to the contact members.

BRIEF DESCRIPTION OF THE DRAWINGS

The invention will be better understood from the following description taken in conjunction with the accompanying drawings, in which.

BEST MODE FOR CARRYING OUT THE INVENTION

Figure 1:
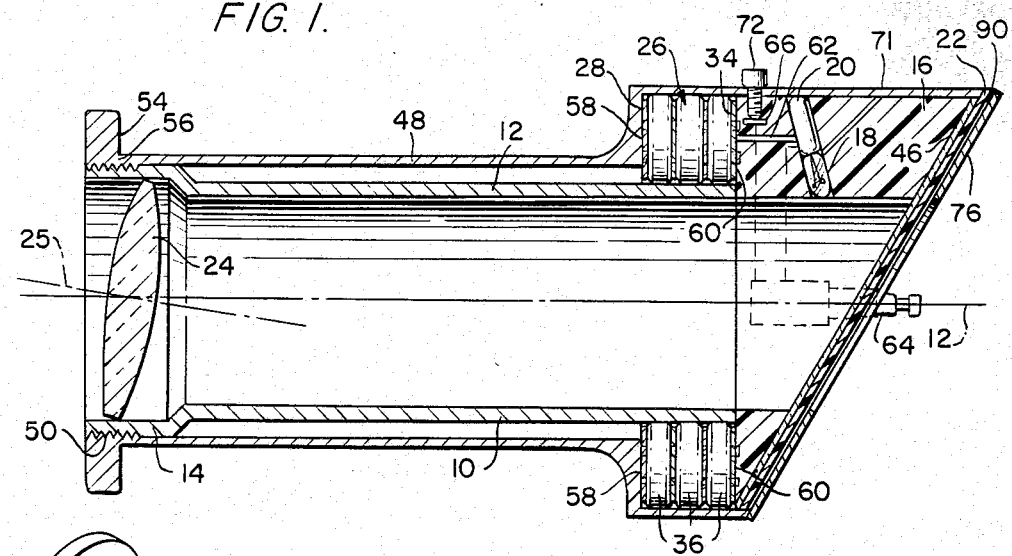
FIG. 1 is a longitudinal sectional view of one embodiment of the ophthalmoscope of the present invention.
Figure 2:
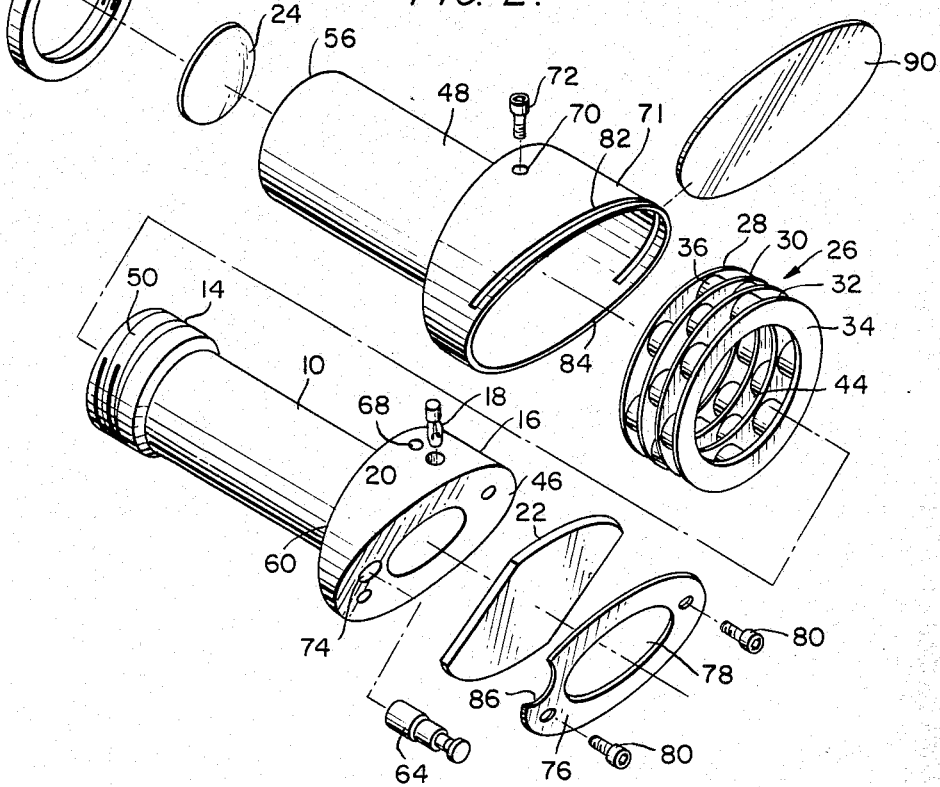
FIG. 2 is an exploded view of the ophthalmoscope illustrated in FIG. 1.

Referring to FIGS. 1 and 2 there is shown one preferred embodiment of the indirect ophthalmoscope of the present invention comprising a generally tubular elongated housing adapted to be held in the examiner's hand with the forward portion of the housing facing the patient and the rearward portion of the housing facing the examiner, an illuminating system within the housing for producing and directing a beam of light onto the fundus of a patient's eye and an optical system for forming an image of the eye fundus which can be conveniently viewed by the examiner. The fundus image is desirably formed along the direct line of sight between the patient's eye and the examiner and is suitable for stereoptic viewing by the examiner using lightweight, head mounted binocular viewing means.

The illuminating and optical systems are mounted within an elongated generally cylindrical optical tube 10 having a central longitudinal axis 12. Tube 10 includes an enlarged diameter, generally cylindrical forward end portion 14 and an enlarged diameter, generally cylindrical rearward end portion 16. The illuminating system includes a light source, such as incandescent bulb 18, disposed within bore 20 in rearward end portion 16 to project generally parallel rays of light onto a semi-transparent mirror 22 which is mounted on and supported by end portion 16. The mirror 22 is oriented at an acute angle to axis 12 which is selected to reflect the incident light rays from bulb 18 along the length of tube 10 to provide illuminating rays to convex lens 24 mounted within forward end portion 14. The illuminating rays are most desirably substantially parallel to axis 12, although rays which diverge only slightly from axis 12 between mirror 22 and lens 24 are acceptable and are encompassed within the term substantially parallel as used herein. By providing lens 24 with substantially parallel or slightly diverging incoming light rays, the lens can establish a substantial focus at or beyond its focal point, which is important to provide sufficient illumination to the eye fundus. Thus, the mirror angle is primarily determined by the angle of the incident light beam from the source and is arranged such that the acute angle between the mirror 22 and the tube axis 12 equals the acute angle between the incident light rays and the mirror 22. In one preferred embodiment the mirror is arranged at an angle of 45° to axis 12 and the incident light beam strikes the mirror at a 45° angle. In other embodiments other angle combinations may be employed, it having been found most practical to arrange mirror 22 at an angle of 30° to 60° to axis 12 and to direct the incident light beam at an angle of 30° to 60° to the mirror. However, it will be appreciated that mirror 22 may be oriented at some other angle as may be desired. Another factor in providing lens 24 with illuminating light rays which are substantially parallel to axis 12 is assuring that optical tube 10 has sufficient length between mirror 22 and lens 24 that light rays which are reflected from mirror 22 in directions other than substantially parallel to axis 12 will be absorbed by the optical tube walls, which are made non-reflecting by anodizing or other treatment to avoid unwanted reflection and glare.

The light rays emitted from the light source are reflected from the semi-transparent mirror 22 along axis 12, which corresponds to the line of sight between the observer and the eye fundus, and is also the optical axis of tube 10. The rays are focused by the convex condensing lens 24, pass through the pupillary aperture of the patient's eye and illuminate the fundus. The point of focus of the illuminating light rays is desirably located during eye examination close to the pupillary aperture, the light rays diverging sharply within the eye to provide a wide angle of illumination for the fundus. Thus, the focal length of the condensing lens 24 is selected to provide a point of focus at a distance from the patient's eye which takes into account the competing considerations of the comfort of the patient, in not placing the examining instrument too close to the eye, and the need to place the instrument close enough to the eye to efficiently gather the fundus image rays leaving the eye. It has been found that a suitable and efficient balancing of these considerations is accomplished by selecting a 28 diopter condensing lens which focuses incoming parallel light rays at a distance of about 35 mm from the lens. However, condensing lenses of other dioptic powers are also suitable.

Figure 8:
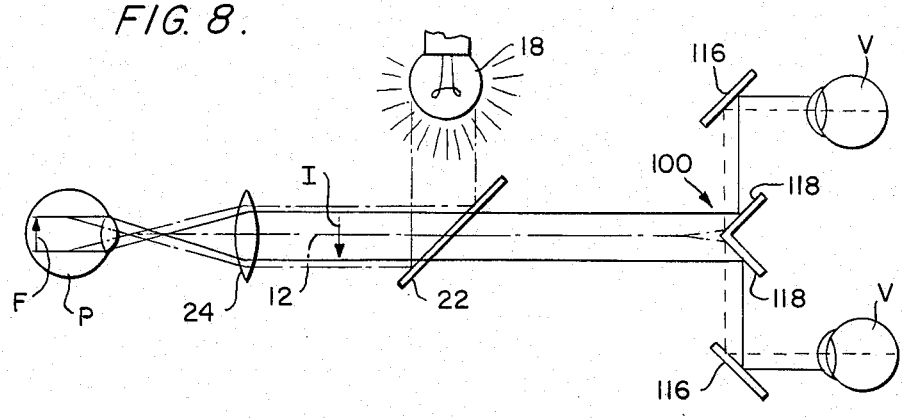
FIG. 8 is a schematic view of the optical beam path in the ophthalmoscope of the present invention.

The light rays comprising the fundus image leave the pup111ary aperture along the line of sight axis 12 between the patient's eye fundus and the observer and pass through the condensing lens 24, which forms a part of the optical as well as the illuminating system, to form the fundus image along the line of sight axis 12. Surface reflections of illuminating light onto lens 24 will significantly interfere with the fundus image unless the lens 24 is mounted so that its optical axis 25 forms a small angle of about 5° to 10° with the optical axis of tube 10. The image of the eye fundus as viewed by an observer sighting along the line of sight axis 12 through mirror 22 and along tube 10 is reversed and inverted. Thus, the image of the eye fundus as represented by image line I in FIG. 8, is also reversed and inverted. If it is desired to view an erect and unreversed image through the ophthalmoscope of the present invention, an image correcting means may be incorporated in or employed in conjunction with the image viewing means to be discussed more fully hereinafter. The image correcting means may take the form of one or a plurality of prisms or a combination of mirrors and prisms, all as is well known in the art.

Figure 3:
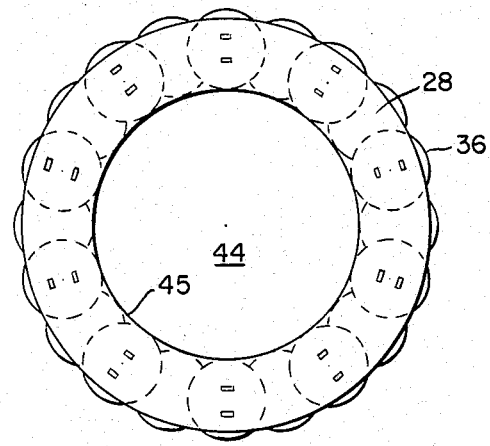
FIG. 3 is a front elevational view of an exemplary battery power unit for use in the ophthalmoscope of the present invention.
Figure 4:
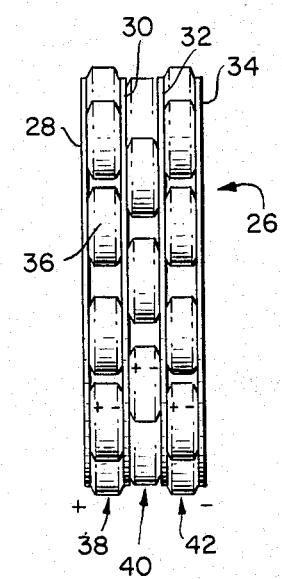
FIG. 4 is a side elevational view of the battery power unit illustrated in FIG. 3.

The light source 18 derives its electrical energy from a compact, lightweight, easily replaceable battery 26 which is configured to be accomodated within the housing of the ophthalmoscope without adversely affecting the easy-to-handle configuration of the ophthalmoscope housing. A preferred form of such a battery 26 is shown in FIGS. 3 and 4 and comprises generally annular shaped metallic contact plates 28, 30, 32, 34 and a plurality of individual cells 36 arranged in spaced relation between each adjacent pair (28,30), (30,32), (32,34) of contact plates. Typically, cells 36 may be flat, cylindrical button or wafer cells wherein the outside container serves as one polar terminal and a generally circular button element projecting from one flat surface of the cell serves as the other polar terminal. The cells may be electrically connected at their terminals to the contact plates by any suitable form of electrical connection, such as by spot welding or use of an electrically conductive adhesive composition. Battery 26 is formed of one or more battery sections arranged in series. Each battery section consists of two contact plates having the desired number of individual cells, depending upon the desired voltage and current characteristics, electrically connected therebetween in parallel. Thus, the illustrated battery 26 consists of three battery sections 38, 40, 42. Section 38 includes contact plates 28 and 30 and a plurality of cells 36 arranged in parallel therebetween, with the positive terminal of each cell 36 electrically connected to plate 28 and the negative terminal of each cell 36 electrically connected to plate 30. Section 40 consists of contact plates 30 and 32 and cells 36 electrically connected therebetween with the positive terminal of each cell 36 connected to plate 30 and the negative terminal connected to plate 32. Section 42 consists of contact plates 32 and 34 and cells 36 electrically connected therebetween with the positive terminal of each cell 36 connected to plate 32 and the negative terminal connected to plate 34. Inasmuch as plate 30 is common to adjacent battery sections 38 and 40 and plate 32 is common to adjacent battery sections 40 and 42, common plates 30 and 32 serve as the electrical connector linking adjacent battery sections in series to form battery 26 having its positive terminal at plate 28 and its negative terminal at plate 34. Batteries having substantially the configuration shown in FIGS. 3 and 4 and employing three battery sections, each including ten conventional button cells (1.5 volts each), such as are available from Union Carbide Corporation under the trade designation EP 675, provide sufficient electrical energy to power an ophthalmoscope light source for illuminating an eye fundus.

Battery pack 26 is annular in configuration with the several battery sections 38, 40, 42 substantially coaxial to define an elongated enclosed central opening 44 therewithin of a generally circular cross-section into which a generally cylindrical support means, such as optical tube 10, can be inserted. For maximum compactness in use it is desirable that opening 44 be configured such that the interior surface 45 of the annular battery 26 substantially conforms to the outer surface of the support means. It will, of course, be appreciated that batteries in accordance with the present invention may be most conveniently supported in any particular application by a support means having an outer surface configuration other than cylindrical. In such a case the elongated enclosed opening 44 may assume a configuration other than cylindrical to conform to the supporting surface. Accordingly, as used herein, the term "annular" as applied to the shape of a surface is not confined to a circularly annular surface but is intended to comprehend any substantially continuous peripheral surface, having any planar configuration, which extends substantially completely around a substantially central opening. Thus, the term "annular" includes closed ring-shaped or circular annular surfaces as were as non-circular peripheral surfaces enclosing triangular, quadrilateral, polygonal or non-regular shaped openings. The term "annular" also includes substantially closed peripheral surfaces.

Referring again to the particularly preferred embodiment of the present invention illustrated in FIGS. 1 and 2 it can be seen that the rearmost surface 46 of enlarged end portion 16 is inclined at an angle to optical axis 12 to permit mounting mirror 22 thereon at the desired angle for providing reflected rays which are substantially parallel to the optical axis 12. Optical tube 10 with battery pack 26 supported thereon is housed within cover 48 with the outer threaded end 50 of forward end portion 14 extending through a central opening in cover 48. End nut 52 threads onto threaded end 50 with the rearward facing surface 54 of nut 52 abutting the forward end 56 of cover 48 to urge cover 48 rearwardly until inner annular shoulder 58 of cover 48 abuts and electrically contacts annular contact plate terminal 28 of battery 26 urging battery 26 rearwardly until annular contact plate terminal 34 abuts forward facing annular shoulder 60 of enlarged end portion 16 and electrically contacts the forwardly projecting end of contact pin 62 embedded in end portion 16. The rearwardly projecting end of contact pin 62 is electrically connected to light bulb 18 which, in turn, is electrically connected to one terminal of switch 64. The other terminal of switch 64 is electrically connected to contact disc 66 embedded at the base of a shallow bore 68 in end portion 16. With cover 48 securely held in place and urged rearwardly by end nut 52, aperture 70 in enlarged head portion 71 of cover 48 aligns with bore 68 to allow an electrically conductive set screw 72 to be threaded into aperture 70 and extend into bore 68 to electrically connect cover 48 and contact disc 66 to close, when switch 64 is closed, the electrical circuit which provides electrical energy from battery 26 to light bulb 18.

Figure 5:
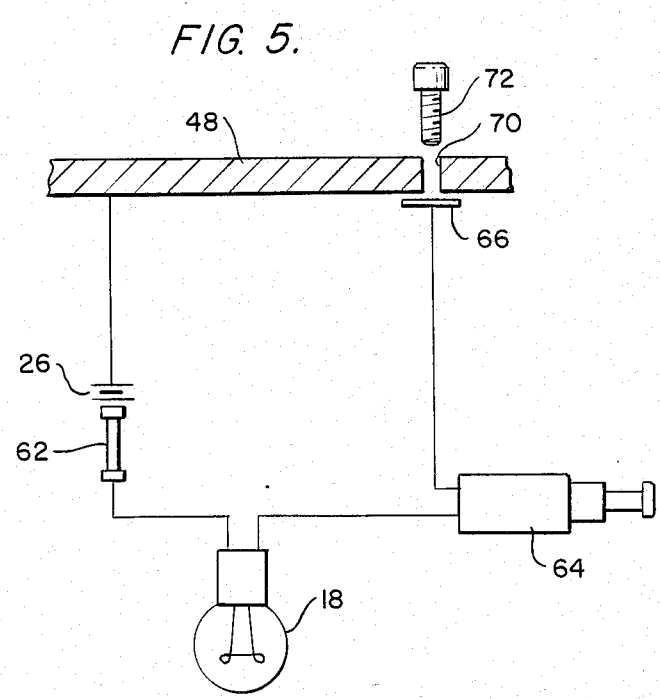
FIG. 5 is an exemplary wiring diagram for the illuminating system of the ophthalmoscope of the present invention.

The electrical circuit is more clearly illustrated in FIG. 5 wherein it can be seen that cover 48 is electrically connected to one polar terminal of battery 26 and that contact disc 66, via switch 64, light bulb 18 and contact pin 62 is electrically connected to the opposite polar terminal of battery 26. The circuit is completed by set screw 72 threadably engaged in aperture 70 to electrically connect cover 48 and contact plate 66. Switch 64 is a conventional ON-OFF switch which has a rheostat control associated with it in order that a single switch can be used for both ON-OFF power control and lamp brightness control.

Switch 64 is mounted in bore 74 formed in inclined surface 46 of end portion 16. End plate cover 76 having a central opening 78 therein overlies a portion of mirror 22 and is mounted to end portion 16 in conventional manner, as with screws 80, with the periphery of its forward facing surface abutting the rearward end 84 of cover 48. End plate cover 76 is notched at 86 to accomodate the rearwardly extending portion of switch 64. If desired, one or more resilient O-rings (not shown) or other well known sealing means can be employed to enhance the fluid-tightness of the ophthalmoscope to permit liquid or gas sterilization of the instrument. Central opening 78 of end plate cover 76 is desirably coaxially arranged with respect to optical axis 12 such that a direct line of sight is established between the physician-observer and the eye fundus along the optical axis 12 through central opening 78, mirror 22, optical tube 10 and lens 24.

The ophthalmoscope of the present invention may, as a further feature, include removably insertable filters 90, such as colored filters which are of great value in diagnostic work. The filters 90 may be of various colors and are so positioned that they are not in the light path of the fundus illuminating light rays and, therefore, do not diminish the illuminating light intensity. However, they are in the fundus image path to the eye of the physician-observer. In a preferred arrangement, end plate cover 76 is positioned rearwardly of mirror 22 to define an axially extending space therebetween for receiving filters 90 which may be inserted therein through slot 82 formed in the upper portion of enlarged head portion 71 immediately adjacent but spaced forwardly of its rearward end 84. In this position filters 90 may be readily changed without interfering with the position or operation of the ophthalmoscope.

Figure 6:
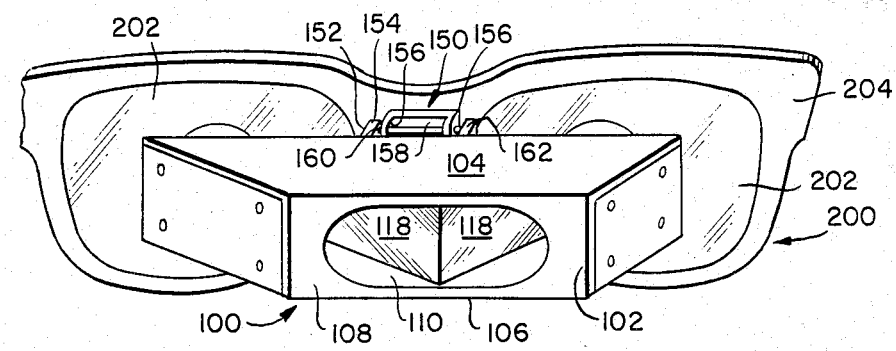
FIG. 6 is a perspective view of an exemplary binocular viewing device mounted on spectacle frames for stereoptic viewing of the fundus image produced by the ophthalmoscope of the present invention.
Figure 7:
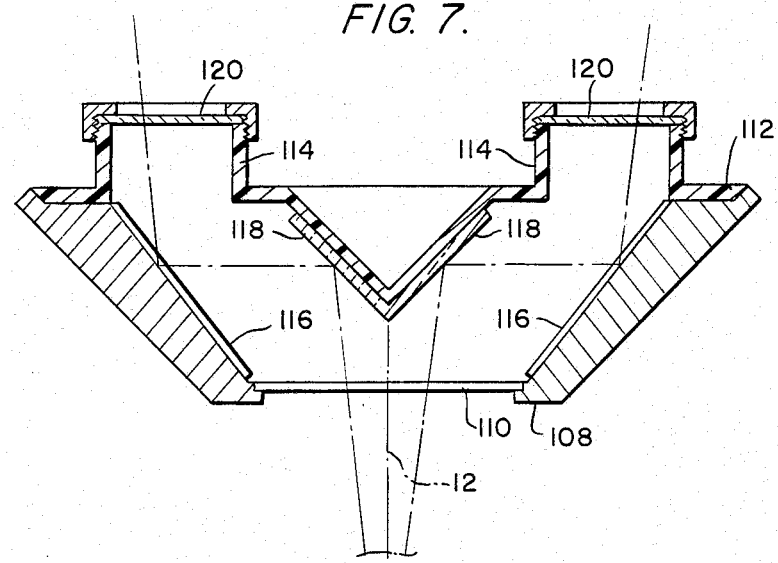
FIG. 7 is a plan view in section through the binocular viewing device illustrated in FIG. 6.

An exemplary binocular viewing means 100 suitable for use in conjunction with the ophthalmoscope of the present invention for reducing the effective interpupillary distance of the observer to permit full stereoptic viewing of the fundus of the eye is illustrated in FIGS. 6 and 7. Viewing means 100 comprises a binocular housing 102 arranged to be secured to a pair of spectacles 200, comprising spectacle lenses 202 held in a rigid frame 204, by hinge attachment means 150. The housing 102 is provided with upper and lower walls 104 and 106 respectively, and a front wall 108 containing a front window 110. The rear wall of the housing 112 is provided with a pair of viewing apertures 114 arranged at a spacing which suits the interpupillary distance between the observer's eyes. The vision of the observer's eyes, indicated schematically at V in FIG. 8, is directed to each of two primary mirrors 116, reflected at substantially right angles by the primary mirrors 116 to right angle-arranged secondary mirrors 118 which are disposed centrally within housing 102, and then by the secondary mirrors 118 at a small angle to intersect at a predetermined distance in front of the housing 102.

Housing 102 is desirably removably affixed to the spectacles frame 204 by hinge attachment means 150 in order that the housing can be used with a personally prescribed frame and corrective lenses. This ensures optimum vision and comfort throughout lengthy examination procedures and long surgical operations and allows a single housing to be used by people with varying defects of vision by securing the housing to any one of a plurality of spectacles. An exemplary hinge attachment means 150 includes an L-shaped mounting bracket 152 having one leg 154 removably affixed to the spectacles frame 204, as by screws (not shown), and the other leg comprising spaced parallel links 156 positioned upon opposite sides of sleeve 158 which is fixedly mounted upon rear wall 112 of housing 102. Extending through the links 156 and sleeve 158 is a pivot pin 160 having a threaded end onto which an adjusting nut 162 is threaded for adjusting the frictional engagement between the links and the sleeve. In this way, the nut can be tightened to provide sufficient frictional engagement between the links and the sleeve that housing 102 can be readily pivoted about pin 160 and positioned in proper relationship before the eyes of the observer when binocular viewing is desired yet easily pivoted about pin 160 to an out-of-the way position when binocular viewing is not desired.

INDUSTRIAL APPLICABILITY

The indirect ophthalmoscope and electrical energy producing means of the present invention are broadly applicable and useful in all aspects of eye examination and surgery and particularly beneficial in instances where compact, lightweight, readily portable instruments are required. Moreover, the electrical energy producing means is widely useful, even in non-ophthalmic light projecting devices, where compact, portable light sources are required, such as to illuminate difficultly accessible locations or in applications where there are severe limitations upon space or upon the shape a light source may assume in order to illuminate remote regions.

When used in instruments for indirect ophthalmoscopy, such as to examine the eye of a patient indicated schematically at P in FIG. 8, switch 64 is operated to turn the light source on and to adjust the intensity of the illumination. Light source 18 projects a light beam (dot-dash lines in FIG. 8) within optical tube 10 to a semi-transparent mirror 22 which, in turn, reflects the light beam along the length of tube 10 in a direction substantially parallel to optical axis 12 to convex lens 24 which converges the light rays through the pupillary aperture and onto the eye fundus, schematically indicated as F in FIG. 8. Illumination is desirably provided by an incandescent bulb 18 powered by an annular battery 26 which is mounted upon the outer surface of tube 10. An instrument having substantially the construction shown in FIGS. 1 and 2 is compact and easy to handle, and may conveniently have a lens to mirror distance of about 10–11 cm and an optical tube diameter of about 4 cm.

In operation the ophthalmoscope is located such that the optical axis 12 of optical tube 10 is aligned between the pupil of the eye to be observed and the observer to form a direct line of sight therebetween. The observer holds the ophthalmoscope in his hand and places it a comfortable distance from the patient's eye with the lens mounted forward end thereof adjacent the eye to permit illuminating light rays from lens 24 to pass into and through the pupillary aperture. The observer places himself in position to sight into and through the semi-transparent mirror 22 mounted at the rearward end of optical tube 10.

The light rays comprising the image of the eye fundus (solid lines in FIG. 8) are focused by lens 24 onto an intermediate image plane indicated schematically as I in FIG. 8 as an inverted and reversed image of the fundus. The observer sights along the optical axis 12 to view the image of the fundus on image plane I using binocular viewers 100 to reduce his effective interpupillary distance (dashed lines in FIG. 8) and permit full stereoptic observation of the fundus.

The binocular viewer 100 includes a right angle mirror 118 aligned such that its apex is along the optical axis 12 and each reflecting surface of the mirror is at 45° to the optical axis 12. The viewer also includes mirrors 116 mounted on each side of mirror 118 which are adapted to deflect the incident light rays at right angles to, respectively, the left and right eyes (V in FIG. 8) of the observer through observing windows 120 in viewing apertures 114. If desired, the fundus image can be erected and/or reversed using conventional image erecting and reversing prisms, mirrors, and the like.

I claim:

1. In an ophthalmoscope for observing the fundus of an eye including a casing having an image receiving aperture and an image viewing aperture, illuminating means including a light source for providing a light beam for illuminating the fundus and lens means for viewing the illuminated fundus, the improvement comprising electrical energy producing means for providing electrical energy to said light source, said electrical energy producing means comprising a substantially annular battery, said battery including:
   (a) first and second substantially annular contact members; and
   (b) a plurality of battery cells arranged in spaced relation and disposed between and electrically connected to said contact members,
said electrical energy producing means adapted to be removably supported on said casing and extending substantially completely around and substantially conforming to the outer surface of a section of said casing and means electrically connecting said light source and said electrical energy producing means.

2. An opthalmoscope, as claimed in claim 1, wherein said battery cells are arranged in parallel with the positive terminals of each of said battery cells being electrically connected to one of said first and second contact members and the negative terminals of each of said battery cells being electrically connected to the other of said contact members.

3. An ophthalmoscope, as claimed in claim 1, wherein said electrical energy producing means comprises a plurality of substantially annular contact members arranged in substantially parallel spaced relation, a plurality of battery cells arranged in spaced relation and disposed between and electrically connected to each pair of adjacent contact members, each pair of adjacent contact members and the battery cells disposed therebetween comprising a battery section, each pair of adjacent battery sections having a common contact member, said battery cells within each section being electrically arranged in parallel with the positive terminals of each of said cells electrically connected to one of said pair of contact members and the negative terminals of each of said cells connected to the other of said pair of contact members, the common contact members of adjacent pairs of battery sections having electrically connected thereto the positive terminals of the battery cells of one of said adjacent battery sections and the negative terminals of the battery cells of the other of said adjacent battery sections, whereby adjacent battery sections are electrically arranged in series.

4. An ophthalmoscope, as claimed in claims 2 or 3, wherein each contact member comprises a generally circular, annular plate-like member enclosing a generally circular opening therewithin.

5. An ophthalmoscope, as claimed in claims 2 or 3, wherein each contact member comprises a generally circular, annular plate-like member enclosing a generally circular opening therewithin and said contact members are substantially coaxial to define a generally cylindrically extending annular battery having a generally cylindrical opening defined therewithin for receiving a section of said casing therein.

6. An opthalmoscope for observing the fundus of an eye comprising:
   a casing adapted to be supported during fundus observation having an image receiving aperture and an image viewing aperture, said apertures disposed along a direct line of sight through said casing;
   a convex lens mounted in said casing near said image receiving aperture;
   fundus illumination means in said casing providing a light beam for illuminating the fundus of an eye, said fundus illumination means including
   a light source for emitting a light beam,
   a semi-transparent mirror mounted near said image viewing aperture, said mirror being oriented to intercept said emitted light beam for reflecting at least a portion of said light beam through said lens onto the fundus of an eye, and
   electrical energy producing means for providing electrical energy to said light source,
said electrical energy producing means comprising a substantially annular battery, said battery including:
   (a) first and second substantially annular contact members; and
   (b) a plurality of battery cells arranged in spaced relation and disposed between and electrically connected to said contact members,
said electrical energy producing means adapted to be removably supported on said casing and extending substantially completely around and substantially conforming to the outer surface of a section of said casing and means electrically connecting said light source and said electrical energy producing means.

7. An ophthalmoscope, as claimed in claim 6, wherein said battery cells are arranged in parallel with the positive terminals of each of said cells electrically connected to one of said first and second contact members and the negative terminals of each of said cells electrically connected to the other of said contact members.

8. An ophthalmoscope, as claimed in claim 6, wherein said electrical energy producing means comprises a plurality of substantially annular contact members arranged in substantially parallel spaced relation, a plurality of battery cells arranged in spaced relation and disposed between and electrically connected to each pair of adjacent contact members, each pair of adjacent contact members and the battery cells disposed therebetween comprising a battery section, each pair of adjacent battery sections having a common contact member, said battery cells within each section being electrically arranged in parallel with the positive terminals of each of said cells electrically connected to one of said pair of contact members and the negative terminals of each of said cells connected to the other of said pair of contact members, the common contact members of adjacent pairs of battery sections having electrically connected thereto the positive terminals of the battery cells of one of said adjacent battery sections and the negative terminals of the battery cells of the other of said adjacent battery sections, whereby adjacent battery sections are electrically arranged in series.

9. An ophthalmoscope, as claimed in claim 7, wherein each contact member comprises a generally circular, annular plate-like member enclosing a generally circular opening therewithin.

10. An ophthalmoscope, as claimed in claim 8, wherein each contact member comprises a generally circular, annular plate-like member enclosing a generally circular opening therewithin.

11. An ophthalmoscope, as claimed in claim 7, wherein each contact member comprises a generally circular, annular plate-like member enclosing a generally circular opening therewithin and said contact members are substantially coaxial to define a generally cylindrically extending annular battery having a generally cylindrical opening defined therewithin for receiving a section of said casing therein.

12. An ophthalmoscope, as claimed in claim 8, wherein each contact member comprises a generally circular, annular plate-like member enclosing a generally circular opening therewithin and said contact members are substantially coaxial to define a generally cylindrically extending annular battery having a generally cylindrical opening defined therewithin for receiving a section of said casing therein.

13. An ophthalmoscope, as claimed in claim 12, wherein said casing comprises an elongated generally cylindrical tubular member having said image receiving aperture adjacent one end thereof and said image viewing aperture adjacent the other end thereof and said battery is supported on said casing with said tubular member received in said generally cylindrical opening.

14. An ophthalmoscope, as claimed in claims 6, 7, 8, 9, 10, 11, 12 or 13 including means in said casing adjacent said image viewing aperture for removably receiving light filters to be interposed along the line of sight for viewing the fundus image.

15. An ophthalmoscope, as as claimed in claims 6, 7, 8, 9, 10, 11, 12, or 13, wherein the convex lens is positioned with its optical axis at an acute angle to the line of sight.

16. An ophthalmoscope, as claimed in claims 8 or 13, wherein said means electrically connecting said light source and said electrical energy producing means includes switch means for selectively interrupting the provision of energy to said light source.

17. An ophthalmoscope, as claimed in claims 8 or 13, wherein said means electrically connecting said light source and said electrical energy producing means includes means for varying the illumination intensity of the light beam emitted by said light source.

18. A light projecting device comprising a casing, a light source for emitting a beam of light in said casing, means associated with said casing for permitting transmission of at least a portion of said light beam out of said casing, and electrical energy producing means for providing electrical energy to said light source, said electrical energy producing means comprising a substantially annular battery, said battery including:
(a) first and second substantially annular contact members; and
(b) a plurality of battery cells arranged in spaced relation and disposed between and electrically connected to said contact members,
said electrical energy producing means adapted to be removably supported on said casing and extending substantially completely around and substantially conforming to the outer surface of a section of said casing and means electrically connecting said light source and said electrical energy producing means.

19. A light projecting device, as claimed in claim 18, wherein said battery cells are arranged in parallel with the positive terminals of each of said cells electrically connected to one of said first and second contact members and the negative terminals of each of said cells electrically connected to the other of said contact members.

20. A light projecting device, as claimed in claim 18, wherein said electrical energy producing means comprises a plurality of substantially annular contact members arranged in substantially parallel spaced relation, a plurality of battery cells arranged in spaced relation and disposed between and electrically connected to each pair of adjacent contact members, each pair of adjacent contact members and the battery cells disposed therebetween comprising a battery section, each pair of adjacent battery sections having a common contact member, said battery cells within each section being electrically arranged in parallel with the positive terminals of each of said cells electrically connected to one of said pair of contact members and the negative terminals of each of said cells connected to the other of said pair of contact members, the common contact members of adjacent pairs of battery sections having electrically connected thereto the positive terminals of the battery cells of one of said adjacent battery sections and the negative terminals of the battery cells of the other of said adjacent battery sections, whereby adjacent battery sections are electrically arranged in series.

21. A light projecting device, as claimed in claims 19 or 20, wherein each contact member comprises a generally circular, annular plate-like member enclosing a generally circular opening therewithin.

22. A light projecting device, as claimed in claims 19 or 20, wherein each contact member comprises a generally circular, annular plate-like member enclosing a generally circular opening therewithin and said contact members are substantially coaxial to define a generally cylindrically extending annular battery having a generally cylindrical opening defined therewithin for receiving a section of said casing therein.

23. A light projecting device, as claimed in claims 18, 19 or 20, wherein said device is an opthalmoscope for observing the fundus of an eye, said casing includes an image receiving aperture and an image viewing aperture and said means for permitting transmission of said light beam out of said casing comprises said image receiving aperture.

* * * * *